United States Patent [19]

Grob et al.

[11] Patent Number: 4,559,332
[45] Date of Patent: Dec. 17, 1985

[54] 20-SPIROXANES AND ANALOGUES HAVING AN OPEN RING E, PROCESSES FOR THEIR MANUFACTURE, AND PHARMACEUTICAL PREPARATIONS THEREOF

[75] Inventors: Jürgen Grob, Giebenach; Jaroslav Kalvoda, Binningen, both of Switzerland

[73] Assignee: Ciba Geigy Corporation, Ardsley, N.Y.

[21] Appl. No.: 598,109

[22] Filed: Apr. 9, 1984

[30] Foreign Application Priority Data

Apr. 13, 1983 [CH] Switzerland .................. 1981/83

[51] Int. Cl.[4] .................................. A61K 31/585
[52] U.S. Cl. .................. 514/175; 260/239.57; 260/239.55 R
[58] Field of Search .................. 260/239.57, 239.55

[56] References Cited

U.S. PATENT DOCUMENTS

3,729,491  4/1973  Klimstra et al. ............... 260/343.6
3,849,404  11/1974  Zawadzki et al. ............. 260/239.57

FOREIGN PATENT DOCUMENTS

1041534  9/1966  United Kingdom ........... 260/239.57

OTHER PUBLICATIONS

Fieser, Louis F. et al., Steroids, Reinhold Publishing Corp., New York, Chapman & Hall, Ltd., London (Adrenocortical Hormones), pp. 708, (1979).
"Chemical Abstracts", vol. 79, (1973), Par. 105471p.

*Primary Examiner*—Elbert L. Roberts
*Attorney, Agent, or Firm*—Michael W. Glynn

[57] ABSTRACT

Steroid compounds of the 20-spiroxane series and their analogues having an open ring E of the formula,

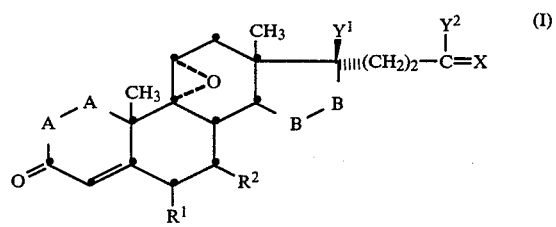

in which
—A—A— represents the group —$CH_2$—$CH_2$— or —CH=CH—,
$R^1$ represents hydrogen, and
$R^2$ represents an α-oriented lower alkoxycarbonyl radical, or
$R^1$ and $R^2$ together represent an α- or a β-oriented methylene radical,
—B—B— represents the group —$CH_2$—$CH_2$— or an α- or β-oriented group

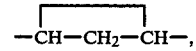

X represents two hydrogen atoms or oxo,
$Y^1$ and $Y^2$ together represent the oxygen bridge —O—, or
$Y^1$ represents hydroxy, and
$Y^2$ represents hydroxy, lower alkoxy or, if X represents $H_2$, also lower alkanoyloxy, and salts of compounds in which X represents oxo and $Y^2$ represents hydroxy, are distinguished as effective aldosterone-antagonists with minimal side-effects and, for that reason, are especially suitable for the treatment of all forms of hyperaldosteronism.

17 Claims, No Drawings

20-SPIROXANES AND ANALOGUES HAVING AN OPEN RING E, PROCESSES FOR THEIR MANUFACTURE, AND PHARMACEUTICAL PREPARATIONS THEREOF

The invention relates to novel 20-spiroxanes and analogue compounds having an open oxygen-containing ring E of the general formula

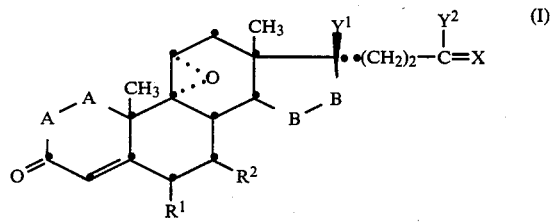

in which
—A—A-represents the group —$CH_2$—$CH_2$— or —CH=CH—,
$R^1$ represents hydrogen, and
$R^2$ represents an α-oriented lower alkoxycarbonyl radical, or
$R^1$ and $R^2$ together represent an α- or a β-oriented methylene radical,
—B—B-represents the group —$CH_2$—$CH_2$— or an α- or β-oriented group

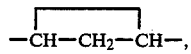

X represents two hydrogen atoms or oxo,
$Y^1$ and $Y^2$ together represent the oxygen bridge —O—, or
$Y^1$ represents hydroxy, and
$Y^2$ represents hydroxy, lower alkoxy or, if X represents $H_2$, also lower alkanoyloxy,
and salts of such compounds in which X represents oxo and $Y^2$ represents hydroxy, that is to say of corresponding 17β-hydroxy-21-carboxylic acids.

The invention relates also to processes for the manufacture of these compounds and to pharmaceutical compositions containing these compounds, and also to processes for the preparation of such compositions. The invention relates also to the therapeutic use of the compounds and compositions mentioned, especially as aldosterone-antagonistic diuretics, and to the corresponding medical method for the treatment of a warm-blooded animal, especially a human, with a therapeutically effective amount of such a compound on its own or in the form of a pharmaceutical composition to cure or alleviate pathological conditions connected with hyperaldeosteronism.

Unless stated otherwise, organic radicals referred to as "lower" in the present disclosure contain at most 7, and preferably from 1 to 4, carbon atoms.

A lower alkoxycarbonyl radical is preferably one derived from an alkyl radical having from 1 to 4 carbon atoms, such as methyl, ethyl, propyl, isopropyl, butyl, isobutyl, sec.-butyl and tert.-butyl; especially preferred are methoxycarbonyl, ethoxycarbonyl and isopropoxycarbonyl. A lower alkoxy radical is preferably one derived from one of the above-mentioned $C_1$-$C_4$ alkyl radicals, especially from a primary $C_1$-$C_4$ alkyl radical; especially preferred is methoxy. A lower alkanoyl radical is preferably one derived from a straight-chain alkyl having from 1 to 7 carbon atoms; especially preferred are formyl and acetyl.

A methylene bridge in the 6,7- and/or 15,16-position is preferably β-oriented.

Preferred compounds of the formula I are those in which $Y^1$ and $Y^2$ together represent the oxygen bridge —O—.

Especially preferred compounds of the formula I are those in which X represents oxo.

Of compounds of the formula I in which $R^1$ represents hydrogen, $R^2$ represents lower alkoxycarbonyl and X represents oxo there are most especially preferred those in which $Y^1$ together with $Y^2$ represents the oxygen bridge —O—.

As already mentioned, 17β-hydroxy-21-carboxylic acids may also be in the form of their salts. There come into consideration especially metal and ammonium salts, such as alkali metal and alkaline earth metal salts, for example sodium, calcium, magnesium and, preferably, potassium, salts, and ammonium salts derived from ammonia or a suitable, preferably physiologically tolerable, organic nitrogen-containing base. As bases there come into consideration not only amines, for example lower alkylamines (such as triethylamine), hydroxy-lower alkylamines [such as 2-hydroxyethylamine, di-(2-hydroxyethyl)-amine or tri-(2-hydroxyethyl)-amine], cycloalkylamines (such as dicyclohexylamine) or benzylamines (such as benzylamine and N,N'-dibenzylethylenediamine), but also nitrogen-containing heterocyclic compounds, for example those of aromatic character (such as pyridine or quinoline) or those having an at least partially saturated heterocyclic ring (such as N-ethylpiperidine, morpholine, piperazine or N,N'-dimethylpiperazine).

Also included amongst preferred compounds are alkali metal salts, especially potassium salts, of compounds of the formula I in which $R^1$ and $R^2$ together represent a methylene group or, especially, $R^1$ represents hydrogen and $R^2$ represents lower alkoxycarbonyl, with X representing oxo and each of $Y^1$ and $Y^2$ representing hydroxy.

Especially preferred compounds of the formula I are, for example, the following:
9α,11α-epoxy-7α-methoxycarbonyl-20-spirox-4-ene-3,21-dione,
9α,11α-epoxy-7α-ethoxycarbonyl-20-spirox-4-ene-3,21-dione,
9α,11α-epoxy-7α-isopropoxycarbonyl-20-spirox-4-ene-3,21-dione,
and the 1,2-dehydro analogue of each of the compounds,
9α,11α-epoxy-6α,7α-methylene-20-spirox-4-ene-3,21-dione,
9α,11α-epoxy-6β,7β-methylene-20-spirox-4-ene-3,21-dione,
9α,11α-epoxy-6β,7β;15β,16β-bismethylene-20-spirox-4ene-3,21-dione,
and the 1,2-dehydro analogue of each of these compounds,
9α,11α-epoxy-7α-methoxycarbonyl-17β-hydroxy-3-oxo-pregn-4-ene-21-carboxylic acid,
9α,11α-epoxy-7α-ethoxycarbonyl-17β-hydroxy-3-oxo-pregn-4-ene-21-carboxylic acid,
9α,11α-epoxy-7α-isopropoxycarbonyl-17β-hydroxy-3-oxo-pregn-4-ene-21-carboxylic acid, 9α,11α-epoxy-17β-hydroxy-6α,7α-methylene-3-oxo-
pregn-4-ene-21-carboxylic acid,
9α,11α-epoxy-17β-hydroxy-6β,7β-methylene-3-oxo-
pregn-4-ene-21-carboxylic acid,
9α,11α-epoxy-17β-hydroxy-6β,7β;15β,16β-bismethy-
lene-3-oxo-pregn-4-ene-21-carboxylic acid, and alkali
metal salts, especially the potassium salt, of each of
these acids, and also a corresponding 1,2-dehydro
analogue of each of the mentioned carboxylic acids
or of a salt thereof,
9α,11α-epoxy-15β,16β-methylene-3,21-dioxo-20-
spirox-4-ene-7α-carboxylic acid methyl ester, ethyl
ester and isopropyl ester,
9α,11α-epoxy-15β,16β-methylene-3,21-dioxo-20-
spiroxa-1,4-diene-7α-carboxylic acid methyl ester,
ethyl ester and isopropyl ester,
and also 9α,11α-epoxy-3-oxo-20-spirox-4-ene-7α-car-
boxylic acid methyl ester, ethyl ester and isopropyl
ester,
9α,11α-epoxy-6β,7β-methylene-20-spirox-4-en-3-one,
9α,11α-epoxy-6β,7β;15β,16β-bismethylene-20-spirox-
4-en-3-one,
and also 9α,11α-epoxy-17β-hydroxy-17α-(3-hydroxy-
propyl)-3-oxo-androst-4-ene-7α-carboxylic acid methyl
ester, ethyl ester and isopropyl ester,
9α,11α-epoxy-17β-hydroxy-17α-(3-hydroxypropyl)-
6α,7α-methylene-androst-4-en-3-one,
9α,11α-epoxy-17β-hydroxy-17α-(3-hydroxypropyl)-
6β,7β-methylene-androst-4-en-3-one,
9α,11α-epoxy-17β-hydroxy-17α-(3-hydroxypropyl)-
6β,7β;15β,16β-bismethylene-androst-4-en-3-one,
including 17α-(3-acetoxypropyl) and 17α-(3-formylox-
ypropyl) analogues of the mentioned androstane com-
pounds,
and also 1,2-dehydro analogues of all the mentioned
compounds of the androst-4-en-3-one and 20-spirox-4-
en-3-one series.

The compounds according to the invention are distin-
guished by favourable biological properties and are,
therefore, valuable pharmaceutical active ingredients.
For example, they have a strong aldosterone-antagonis-
tic action in that they reduce and normalise unduly high
sodium retention and potassium excretion caused by
aldosterone. They therefore have, as potassium-saving
diuretics, an important therapeutic application, for ex-
ample in the treatment of hypertension, cardiac insuffi-
ciency or cirrhosis of the liver.

20-Spiroxane derivatives having an aldosterone-
antagonistic action are known, cf., for example, Fieser
and Fieser: Steroids; page 708 (Reinhold Publ. Corp.,
New York, 1959) and British Patent Specification No.
1,041,534; also known are analogously active 17β-
hydroxy-21-carboxylic acids and their salts, cf., for
example, U.S. Pat. No. 3,849,404. Compounds of this
kind that have hitherto been used in therapy, however,
have a considerable disadvantage in that they always
possess a certain sexual-specific activity which has trou-
blesome consequences sooner or later in the customary
long-term therapy. Especially undesirable are the trou-
blesome effects that can be attributed to the anti-andro-
genic activity of the known anti-aldosterone prepara-
tions.

It has now been found that the above-characterised
9α,11α-epoxy compounds of the formula I surprisingly
exhibit these undesirable side-effects to a substantially
lesser degree although they completely retain the
favourable anti-aldosterone action of compounds that
have an analogous structure but that are not substituted
in the 9,11-position. Thus, for example, 9α,11α-epoxy-
6β,7β-methylene-20-spirox-4-ene-3,21-dione displays in
adrenal-ectomised male rats in the Kagawa test [Ka-
gawa et al.: Proc. Soc. Exptl. Biol. Med. (N.Y.), 115,
837–840 (1964)], in the entire dosage range of from 1 to
10 mg/kg which was tested, an aldosterone-antagonistic
activity that is equally as great as, if not greater than,
that of the corresponding 9,11-unsubstituted compari-
son substance 6β,7β-methylene-20-spirox-4-ene-3,21-
dione (J. F. Zawadzki et al.: U.S. Pat. No. 3,849,404). In
contrast, however, in a specific quantitative test in vitro
in which, as a measure of the antiandrogenic action, the
binding of the test substance to androgen-receptors in
homogenates of ventral prostate glands of rats is mea-
sured, the binding of the former compound is found to
be approximately 20 times (after a 2-hour test period) to
as much as 27 times (after a 20-hour test period) weaker
than in the case of the above-mentioned comparison
compound.

The chemical names of the compounds of the formula
I and of analogue compounds having the same charac-
teristic structural features are derived according to
current nomenclature in the following manner: for com-
pounds in which $Y^1$ together with $Y^2$ represents —O—,
from 20-spiroxane (for example a compound of the
formula I in which X represents oxo and $Y^1$ together
with $Y^2$ represents —O— is derived from 20-spiroxan-
21-one); for those in which each of $Y^1$ and $Y^2$ represents
hydroxy and X represents oxo, from 17β-hydroxy-17α-
pregnene-21-carboxylic acid; and for those in which
each of $Y^1$ and $Y^2$ represents hydroxy and X represents
two hydrogen atoms, from 17β-hydroxy-17α-(3-
hydroxypropyl)-androstane. Since the cyclic and open-
chain forms, that is to say lactones and 17β-hydroxy-21-
carboxylic acids and their salts, respectively, are so
closely related to each other that the latter may be
considered merely as a hydrated form of the former,
there is to be understood hereinbefore and hereinafter,
unless specifically stated otherwise, both in end prod-
ucts of the formula I and in starting materials and inter-
mediates of analogous structure, in each case all the
mentioned forms together.

The compounds of the formula I characterised at the
beginning can be manufactured by processes analogous
to those known per se, for example as follows:

(a) a compound of the formula

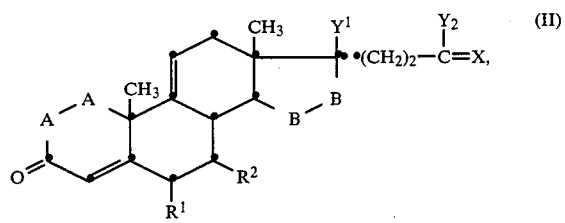

in which A—A, B—B, $R^1$, $R^2$, X, $Y^1$ and $Y^2$ have
the meanings given above, is treated with a peroxy
acid, or (b) a compound of the formula

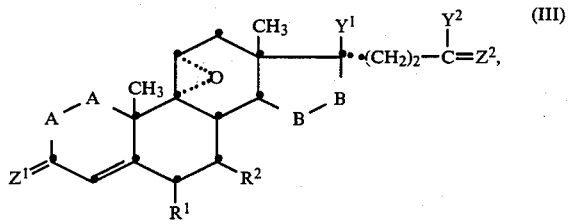

(III)

in which A—A, B—B, $R^1$, $R^2$, $Y^1$ and $Y^2$ have the meanings given above and at least one of the symbols $Z^1$ and $Z^2$ represents hydroxy together with hydrogen and the other has the same meaning or represents oxo or, in the case of the symbol $Z^2$, may also represent two hydrogen atoms, is treated with an oxidising agent, or (c) for the manufacture of a compound in which $Y^1$ represents hydroxy and the other symbols have the meanings given above, a compound of the formula

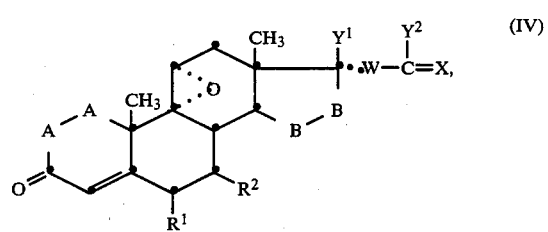

(IV)

in which A—A, B—B, $R^1$, $R^2$, X and $Y^2$ have the meanings given above, $Y^1$ represents hydroxy and W represents a group —CH=CH— or —C≡C—, is hydrogenated to saturate the multiple bond in the side chain, or (d) for the manufacture of a compound of the formula I in which $Y^1$ and $Y^2$ together represent the oxygen bridge —O— and the other symbols have the meanings given above, a compound of the formula

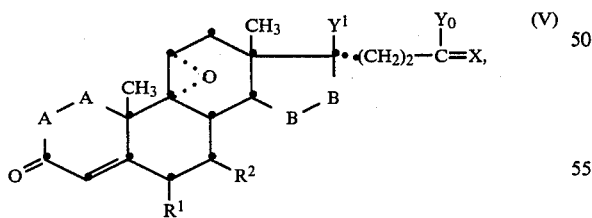

(V)

in which A—A, B—B, $R^1$, $R^2$ and X have the meanings given above, $Y^1$ represents hydroxy and $Y_o$ represents a leaving group, is cyclised with the group $Y_o$ being removed, or (e) for the manufacture of a compound of the formula I in which $R^1$ represents hydrogen and $R^2$ represents a lower alkoxycarbonyl group and the other symbols have the meanings given above, a compound of the formula

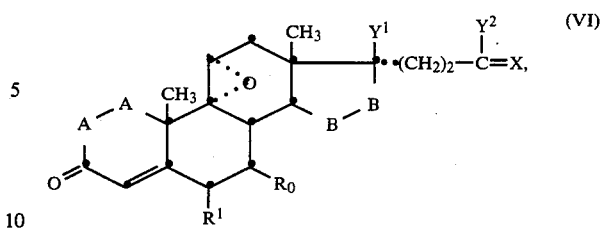

(VI)

in which A—A, B—B, X, $Y^1$ and $Y^2$ have the meanings given above, $R^1$ represents hydrogen and $R_o$ represents free carboxy, or a reactive derivative or salt of such a compound, is converted into an ester, or (f) for the manufacture of a compound in which $R^1$ and $R^2$ together represent a methylene bridge and the other symbols have the meanings given above, the methylene group is added to a compound of the formula

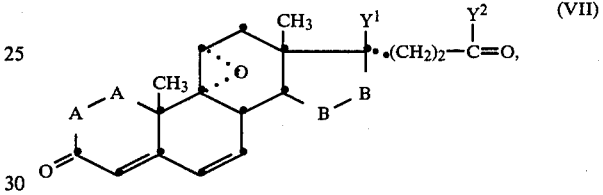

(VII)

in which A—A, B—B, $Y^1$ and $Y^2$ have the meanings give above, and, if desired, (g) a resulting compound of the formula I in which —A—A— represents —CH$_2$—CH$_2$— is treated with a dehydrogenation agent to introduce the 1,2-double bond, and/or (h) a resulting compound of the formula I in which each of $Y^1$ and $Y^2$ represents a hydroxy group is cyclised by removing the elements of water to form a compound of the formula I in which $Y^1$ and $Y^2$ together represent the oxygen bridge, and/or (i) a resulting compound of the formula I in which X represents two hydrogen atoms is oxidised to a corresponding compound in which X represents oxo, and/or (j) in a resulting compound of the formula I in which X represents two hydrogen atoms and each of $Y^1$ and $Y^2$ represents a free hydroxy group the terminal hydroxy group is acylated, and/or (k) a resulting compound of the formula I in which X represents oxo, $Y^1$ represents hydroxy and $Y^2$ represents hydroxy or lower alkoxy, or the two together represent the oxygen bridge —O—, is converted into a salt of the corresponding 17β-hydroxy-21-carboxylic acid of the formula I in which X represents oxo and each of $Y^1$ and $Y^2$ represents hydroxy, and/or such a salt is converted into the free acid and/or the free acid or a salt thereof is converted into a lower alkyl ester.

Process variant (a), i.e. the epoxidation of the 9(11)-double bond, is carried out in a manner known per se by treating the starting material of the formula II with a peroxy acid, preferably an organic peroxy acid, for example an aliphatic peroxy acid, such as, especially, performic acid or peracetic acid, or preferably an aromatic peroxy acid. Of the last-mentioned acids there is advantageously used perbenzoic acid or a substituted perbenzoic acid, such as m-chloroperbenzoic acid or monoperoxyphthalic acid (perphthalic acid). The reaction is carried out especially in an inert organic solvent, for example, in an alkane, such as pentane, hexane or heptane, a halogenated lower alkane, such as, especially, methylene chloride, chloroform or 1,2-dichloroethane, or an open-chain or cyclic ether, such as, especially, diethyl ether, dioxan or tetrahydrofuran, or an appropriate mixture thereof. The reaction temperature should not, as a rule, exceed the temperature at which the spontaneous decomposition of the reactant proceeds more rapidly than the epoxidation reaction, and the reaction is carried out especially at room temperature or, preferably, below that to approximately $-20°$ C., more especially at from $-10°$ to $+10°$ C.

Starting materials of the formula II can, if they are not known, be manufactured by processes analogous to those known per se, for example analogously to one of the process variants (b)-(k) described hereinbelow or a combination thereof, starting from known starting materials, for example correspondingly substituted 17-oxo derivatives of the androstane series, by the conventional formation of the 3-hydroxypropyl side chain or the spiro ring. Alternatively, a compound that is analogous to a compound of the formula I but that contains an 11α- or 11β-hydroxy group in place of the 9,11-epoxy ring can be dehydrated; the 11-hydroxy compound can be obtained, for example, by microbiological hydroxylation of a 9,11-unsubstituted compound.

Process variant (b) is likewise carried out in a manner known per se using conventional oxidising agents and oxidation processes that are customary for the conversion of a hydroxy group into an oxo group. As preferred oxidising agents there are used compounds of hexavalent chromium, such as chromium trioxide, chromic acid and their metal salts, especially alkali metal salts, and as preferred reaction medium there are used lower alkanecarboxylic acids, such as acetic and propionic acid, or pyridine or acetone, optionally with dilution with a halogenated lower alkane, such as dichloromethane or chloroform. The reaction conditions can be finely adapted to the specific character of the hydroxy group in the starting material and of the oxo group in the product: for the oxidation of an allylic 3-hydroxy group mild conditions, such as cooling to a temperature below room temperature, for example to approximately $-10°$ to $+10°$ C., are preferred; for the oxidation to the carboxy group, whether it be the free or the lactonised carboxy group, more energetic conditions are expedient, such as prolonged reaction time, reaction temperatures in the range of or above (up to approximately 50° C.) room temperature and/or aqueous sulphuric acid as solvent for the oxidising agent (for example in the form of an 8N solution as so-called Jones reagent). Alternatively, the oxidiation of an allylic 3-hydroxy group can also be carried out with manganese dioxide in a halogenated lower alkane, such as chloroform, at temperatures of from room temperature to the boiling temperature of the reaction mixture, or with aluminium isopropoxide and a ketone, such as, especially, acetone or cyclohexanone, at temperatures of from room temperature to the boiling temperature of the mixture.

Starting materials of the formula III can, if they are not known, be obtained by processes of steroid chemistry that are known per se, for example by the methods described under process variants (a) and/or (c)-(k), and by appropriate combination thereof. Thus, for example, a starting material of the formula III in which $Z^1$ represents oxo and each of $Y^1$, $Y^2$ and $Z^2$ represents hydroxy (the last-mentioned symbol containing, in addition, a hydrogen atom) is obtained by reacting a corresponding 17-oxo compound, while temporarily protecting the 3-oxo group, with an organometal derivative of the formula

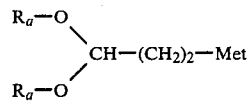

in which Met represents an alkali metal or the halomagnesium group of a corresponding Grignard reagent, and each $R_a$ represents lower alkyl or the two together represent $CH_2$-$CH_2$ or trimethylene, and removing the oxo-protecting groups. The resulting product is present as a mixture of several tautomeric, in part also hydrated, forms corresponding to the partial formulae

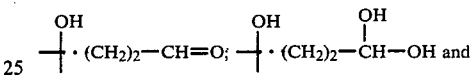

(A)            (B)

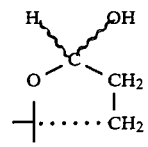

(C)

which, however, behave uniformly in oxidation. Compounds of the formula III in which $Z^1$ represents —OH together with hydrogen are obtained whenever a corresponding 3-oxo compound is subjected to the action of a customary reducing agent, for example simultaneously with the 21-formyl in the reduction of the last-mentioned 21-carbaldehyde with a complex hydride.

Process variant (c) also is carried out in a manner known per se using conventional hydrogenation agents under generally known reaction conditions of catalytic hydrogenation. The reaction is carried out with hydrogen gas at normal or elevated pressure under conditions of heterogeneous or homogeneous catalysis. Especially suitable as catalysts for the former are finely divided metals, for example Raney metals, such as Raney nickel, or nobel metals, such as palladium, platinum or rhodium, which are optionally distributed on a carrier, such as calcium carbonate or barium sulphate. For homogeneous catalysis there are used especially complex rhodium compounds, for example tris(triphenylphosphine)-rhodium(I) chloride. The conditions are to be so chosen that the 1,2- and/or 4,5-double bond is not reduced at the same time.

Starting materials of the formula IV can, if they are not known, be obtained by processes analogous to those of steroid chemistry that are known per se, for example by the methods described under process variants (a), (b) and/or (d) to (k), and by advantageous combination thereof. Thus, for example, a starting material of the formula IV in which W represents the radical —C≡C— is obtained by reacting a suitable 17-oxo compound with an ethynyl-organometal compound, especially an ethynylalkali metal compound, for example sodium or potassium acetylide or, especially, lithium acetylide. In the latter case, it is especially advantageous to use the lithium acetylide in the form of its complex with ethylenediamine. The ethynyl radical introduced can then be carboxylated in a second step by exchanging the terminal hydrogen atom in it for a carboxy group by treatment with a Grignard compound and subsequent reaction of the resulting ω-magnesium halide with carbon dioxide. The 3-oxo group is, as a rule, protected in the usual manner during this reaction. Alternatively, a suitable organometal derivative of propiolic acid can also be used in analogous manner.

In a purely formal sense, irrespective of the reaction mechanism, process variant (d) is effected by simultaneously removing the leaving group $Y_o$ and the hydrogen atom of the 17β-hydroxy group $Y^1$, with the oxygen bridge —O— being formed. When carrying out the reaction in practice, there are used processes analogous to those known per se in organic chemistry that are customary for closing a saturated furan ring, whilst taking into account in each case the specific properties of the leaving group $Y_o$ when choosing the reaction conditions and reactants.

A preferred leaving group $Y_o$ in compounds of the formula V in which X represents oxo is an amino group Am. The amino group Am is preferably a tertiary amino group, especially a di-lower alkylamino group, such as, above all, the dimethylamino and diethylamino group, and forms with the adjacent carbonyl group an optionally N,N-disubstituted 21-carboxamide grouping —C(=O)—Am in which Am has the meaning given above. The conversion of such a starting material into a lactone of the formula I in which $Y^1$ and $Y^2$ together represent the oxygen bridge —O— and X represents oxo is effected in a manner known per se by acidic agents, especially by treatment with an acidic ion exchanger in H-cycle. The amidic starting material can be manufactured in a manner known per se, for example by reacting a corresponding 17-oxo compound, while temporarily protecting the 3-oxo group in conventional manner (for example as ketal or thioketal), in dimethylsulphonium methylide, for example in accordance with the process described in U.S. Pat. No. 3,320,242, and condensing the resulting 17β,20-epoxy-17α-methylsteroid in a manner known per se with the α-carbanion of an N,N-di-lower alkyl acetamide (or an N,N-di-lower alkyl acetamide metallated at methyl by an alkali metal, such as sodium or lithium).

Another advantageous leaving group $Y_o$, which is suitable especially for compounds in which X represents two hydrogen atoms, in a quaternary ammonium group Am+ in the form of the base; the group Am+ is preferably a tri-lower alkylammonium group, such as, especially, the trimethylammonium group. The cyclisation of the quaternary base of the formula V in which X represents two hydrogen atoms and $Y_o$ represents Am+OH− to form a compound of the formula I in which $Y^1$ and $Y^2$ together represent the oxygen bridge is effected by heating the base, optionally in a high-boiling organic solvent, such as ethylene glycol, to decomposition temperature. The corresponding starting material can be manufactured in a manner known per se. For this purpose, a corresponding 17-oxo compound is treated, while temporarily protecting the 3-oxo group in conventional manner, with an organometal compound of the formula $R_c$—$(CH_2)_3$—M in which M represents the grouping MgX in which X is a halogen atom, or represents an alkali metal ion, especially a lithium ion, and $R_c$ represents a di-lower alkylamino group, preferably the dimethylamino group. A 17β-hydroxy-17α-(3-di-lower alkylaminopropyl) compound produced in that manner is then converted into a corresponding quaternary tri-lower alkylammonium salt by the addition of a lower alkyl ester of a strong acid, for example a lower alkyl sulphate or a lower alkyl halide, such as, especially, methyl iodide. From that salt the corresponding quaternary base is freed by treatment with a strong base, preferably a metal hydroxide, for example silver hydroxide, or an alkali metal or alkaline earth metal hydroxide, such as potassium, sodium or barium hydroxide.

Another advantageous leaving group $Y_o$ in compounds of the formula V in which X represents two hydrogen atoms is a reactive esterified hydroxy group. The ester-forming component is, for example, an oxygen-containing inorganic acid, such as sulphuric acid, sulphurous acid, phosphoric acid, phosphorous acid or a substitution derivative thereof in which one or more of the hydroxy groups has been replaced by halogen, especially chlorine (i.e. an acid radical of the type $ClSO_2$—, $ClSO$—, $Cl_2P$—, $Cl_2P(=O)$— or $Cl_4P$—), or an oxygen-free inorganic acid, especially a hydrohalic acid, such as hydrochloric, hydrobromic or hydriodic acid, or alternatively a strong organic acid, for example oxalic acid or, especially, a sulphonic acid, such as an aliphatic or aromatic carbocyclic sulphonic acid, for example, especially, methane-, ethane- or trifluoromethane-sulphonic acid and benzene-, p-toluene- or p-bromobenzene-sulphonic acid, respectively. The cyclisation by removal of such a reactive esterified hydroxy group is effected by treatment with an inorganic or organic basic agent. Inorganic basic agents for this purpose are, for example, hydroxides of alkali metal and alkaline earth metals, such as sodium or potassium and barium or calcium, respectively, and salts thereof with weak inorganic or organic acids, such as, especially, carbonates and bicarbonates, and acetates and formates, respectively. Organic basic agents for this purpose are, for example, tertiary bases of aliphatic character, such as tertiary amines derived from lower alkyl and benzyl radicals (for example triethylamine, benzyldimethylamine, diisopropylethylamine, diisopropylbenzylamine, dibenzylmethylamine or dimethylbutylamine) and their heterocyclic saturated analogues (for example N-methylpyrrolidine, N-methylpiperidine, N-benzylpiperidine or N,N'-dimethylpiperazine), or especially aromatic heterocyclic bases, such as pyridine and its C-methylated analogues (for example collidine) or quinoline. An especially advantageous method of carrying out this process variant consists of removing a reactive esterified hydroxy group, formed in the reaction mixture, in situ, that is to say immediately after it has been produced in the same reaction medium by esterification of the terminal hydroxy group (i.e. the group denoted by the symbol $Y^2$) in a compound of the formula I by means of a reactive acid derivative in a basic medium. A reactive acid derivative is especially an acid halide, such as an acid chloride, which is derived from one of the above-mentioned oxygen-containing inorganic and organic acids. As a typical reactant of this type there is preferred methane-sulphonyl chloride and, most especially, p-toluene-sulphonyl chloride, and, as the reaction medium, there comes into consideration, above all, an aromatic heterocyclic base, such as pyridine. In this manner, end products of the formula I in which X represents two H atoms and each of $Y^1$ and $Y^2$ represents hydroxy are cyclised to end products of the formula I in which X represents two H atoms and $Y^1$ together with $Y^2$ represents —O—.

Process variant (e) is also carried out in a manner known per se. The conversion of the acid of the formula VI into the desired ester of the formula I is usually effected by one of the numerous conventional esterification methods, for example by treatment with a lower alkanol or a reactive derivative thereof, optionally in the presence of catalysts, especially acidic catalysts, and/or agents that remove water, for example a symmetrically substituted carbodiimide, such as, especially, N,N'-dicyclohexyl carbodiimide. Of the acidic catalysts there come into consideration above all strong inorganic acids, such as sulphuric, phosphoric and perchloric acid, and also organic sulphonic acids, such as methane-, benzene- or p-toluene-sulphonic acid; the corresponding alcohol is used in excess, in most cases simultaneously as solvent. Alternatively, it is also possible to esterify in a manner known per se with a diazoalkane, above all diazomethane, or convert the free acid into a reactive derivative thereof, such as a chloride or anhydride, for example a mixed anhydride with trifluoroacetic acid, and react that derivative with the corresponding lower alkanol. Starting materials of the formula VI, if they are not known, are manufactured by processes analogous to those that are known per se, for example by adding hydrocyanic acid to the 6,7-double bond of a suitable 3-oxo-4,6-diene compound (see below) and by conventional conversion of the cyano group into a carboxy group (for example by hydrolysis or by reduction to the formyl group and subsequent oxidation).

Process variant (f) is also carried out in a manner known per se by processes analogous to those conventionally used for adding the methylene group to a double bond. The addition is effected, for example according to a preferred variant, by reacting a 6,7-dehydro compound of the formula VII with a dimethyloxosulphonium methylide. This variant also has the considerable advantage that it has a very high stereospecificity and provides predominantly 6,7-methylene compounds of one configuration, in most cases the α-configuration, of the methylene group. The reaction is advantageously carried out, for example, by bringing together, under an inert gas, such as in a nitrogen atmosphere, and with the exclusion of moisture, a mineral oil dispersion of sodium hydride and trimethylsulphoxonium iodide and adding dimethyl sulphoxide, whereupon the formation of the dimethyloxosulphonium methylide takes place. To this reagent which has been manufactured in situ there is added the 6,7-unsaturated steroid starting material in a molar ratio (reagent:steroid) of approximately from 1:1 to 5:1. The reaction is left to proceed at approximately room temperature and the reaction mixture is treated with water, after which the steroid is isolated according to customary methods. In such end products, which contain alkali-sensitive groups, such as lactone or ester groups, the decomposition of the reaction mixture is advantageously to be steered in such a manner that the pH remains as far as possible in the neutral or weakly acidic range. This method is also suitable for introducing the methylene group into various intermediates in the manufacture of the starting materials of the formulae II to VII. The starting materials of the formula VII required for this variant can, if they are not known, be obtained by processes analogous to those known per se, for example by removal of water (dehydration) from the corresponding 11α- or 11β-hydroxy compounds or by dehydrogenation of corresponding 6,7-saturated intermediates.

According to the end product-end product conversion (g), which may be carried out if desired, 1,2-saturated compounds are dehydrogenated in a manner known per se to the corresponding 1,2-dehydro derivatives. It is possible to use for this purpose biological dehydrogenation methods, for example to dehydrogenate by means of the microorganisms *Corynebacterium simplex* or *Septomyxa affinis* or their enzyme systems, or to treat with selenium dioxide in an organic solvent, for example tert.-butyl alcohol. Preferably, however, dehydrogenation is carried out with 2,3-dichloro-5,6-dicyano-1,4-benzoquinone over several, for example from 6 to 24, hours and optionally at boiling temperature, in organic solvents, for example aromatic hydrocarbons, such as benzene or xylene, lower aliphatic alcohols, such as ethanol, propanol or tert.-butyl alcohol, lower aliphatic ketones, such as acetone or 2-butanone, aliphatic esters, such as ethyl acetate, or cyclic ethers, such as dioxan or tetrahydrofuran.

The cyclisation of an open-chain end product to a cyclic end product according to process variant (h), which may be carried out if desired, is also effected in a manner known per se. Cyclisation of compounds of the formula I in which X represents two hydrogen atoms is effected, for example, in the manner described in process variant (d). End products of the formula I in which X represents oxo and each of $Y^1$ and $Y^2$ represents hydroxy, that is to say free 17β-hydroxy-21-carboxylic acids, are cyclised (lactonised) in a manner known per se by treating them, for example, with a water-removing agent, for example acetic anhydride, anhydrous copper sulphate, molecular sieves or dicyclohexyl carbodiimide, in an inert organic solvent. Lactonisation may also occur spontaneously, especially under acidic conditions and/or at elevated temperature, and is completed, for example, by azeotropic water removal.

The oxidation of the methylene group in the spiro ring E to the carbonyl group in accordance with process variant (i), which may be carried out if desired, is also effected by means of methods that are known per se for the oxidation of a tetrahydrofuran ring to the corresponding lactone ring. For this purpose there are used especially compounds of hexavalent chromium and the reaction is carried out under conditions analogous to those described above, for example, under process variant (b) for the oxidation of corresponding open-chain compounds in which $Y^2$ represents hydroxy and X represents two hydrogen atoms to free carboxylic acids.

Process variant (j), which may be carried out if desired, is effected in accordance with generally known customary esterification processes, preferably by treatment with a lower alkanoic acid, such as, especially, formic acid, on its own, or alternatively with a reactive derivative thereof, such as an anhydride or halide, especially the chloride, preferably in the presence of an organic base, especially a tertiary amine, such as triethylamine, dimethylbenzylamine or N,N-dimethylaniline, a saturated tertiary heterocyclic base, such as N-ethylpiperidine or N,N'-dimethylpiperazine, or an aromatic heterocyclic base, such as quinoline, collidine, lutidine and, above all, pyridine. It is also possible to employ, in addition, inert aprotic organic solvents as the reaction medium.

The conversions in accordance with process variant (k), which may be carried out if desired, are carried out by means of generally known, conventional methods.

Resulting lactones and 22-esters can be converted in a manner known per se into the corresponding 17β-hydroxy-21 -carboxylic acids and salts thereof, for example by hydrolysing them with an alkali metal or alkaline earth metal base, whereupon these are optionally freed, if the free acid is desired, by acidifying.

As alkali metal and alkaline earth metal bases there are used, for example, corresponding hydroxides, such as sodium and, especially, potassium hydroxide, carbonates, such as sodium and potassium carbonate, or bicarbonates, such as sodium and potassium bicarbonate; as reaction medium there are advantageously used mixtures of water and one or more organic solvents, preferably those which are miscible with water, for example lower alkanols, such as methanol, ethanol or isopropyl alcohol, cyclic ethers, such as tetrahydrofuran or dioxan, lower alkanones, such as acetone or 2-butanone, or lower alkyl amides of lower aliphatic carboxylic acids and, among these, especially N,N-dimethylformamide. Preferably, not more than an equivalent amount of the base is used and energetic reaction conditions which could impair other oxygen functions are avoided. If an ester group is present in the 7-position, it can, as a rule, be retained intact under the mild conditions described above since it is hydrolysed considerably more slowly than the esterified or lactonised 21-carboxy group.

The alkali metal and alkaline earth metal salts obtained in that manner can be converted into the corresponding free 17β-hydroxy-21-carboxylic acids by acidifying a solution or suspension of a salt in water or in a water-containing organic solvent. The salts can also be converted into esters, for example with a di-lower alkyl sulphate or lower alkyl halide. Free 17β-hydroxy-21-carboxylic acids can, if desired, also be converted into salts by treatment with a corresponding base, for example into ammonium salts and salts of organic bases, or alternatively esterified, for example in a manner described under (e).

The invention relates also to those forms of the above processes in which a compound obtainable as an intermediate at any stage is used as starting material and the remaining steps are carried out, or in which a starting material is formed under the reaction conditions.

Pharmaceutical preparations of the present invention containing a compound of the formula I, or a salt thereof, can be used especially for the treatment of hyperaldosteronism of very varied forms. They contain an effective amount of the active ingredient on its own or in admixture with inorganic or organic, solid or liquid, pharmaceutically acceptable carriers and, if desired, also in admixture with other pharmacologically or therapeutically valuable substances, and are suitable especially for enteral, for example oral or rectal, administration or for parenteral administration.

Unless more specific information is given, the term "active ingredient" is intended throughout the following text to mean a compound of the formula I, or a salt thereof, as defined at the beginning.

The present invention relates especially to pharmaceutical compositions containing as active ingredient a compound of the formula I (including salts) according to the invention in the form of a sterile and/or isotonic aqueous solution, or alternatively in admixture with at least one solid or semisolid carrier.

The present invention relates also to medicaments, and especially to medicaments in the form of dosage units, which contain at least one of the active ingredients according to the invention on its own or in admixture with one or more carriers, especially those in solid form.

The invention relates especially to medicaments in the form of tablets (including tablets for sucking, granules and pastilles), dragées, capsules, pills, ampoules, dry-filled phials or suppositories containing the above-defined active ingredient on its own or in admixture with one or more carriers.

As a special form of these pharmaceutical compositions and medicaments according to the invention there come into consideration also those which contain, in addition to the aldosterone-antagonistic compound of the formula I (including salts) according to the invention, which is referred to as component A in this context, also a diuretic component B which is non-specific with regard to electrolytes.

There come into consideration as such a diuretic component B which is non-specific with regard to electrolyte excretion conventional "classic" diuretics or mixtures thereof which increase diuresis both by renal and by extrarenal action on tissue, especially substances having an inhibiting action on the reabsorption in the tubules, such as saluretics or ethacrynic acid and analogues thereof. Especially suitable as the electrolyte-non-specific component B are benzothiadiazine derivatives, such as thiazides and hydrothiazides, also benzenesulphonamides, phenoxyacetic acids, benzofuran-2-carboxylic acids and 2,3-dihydrobenzofuran-2-carboxylic acids. The electrolyte-non-specific component B may consist of a single active ingredient or an advantageous combination of several active ingredients, it being possible also for the active ingredients to belong to several of the groups of substances mentioned. Most especially, there come into consideration as the component B the following conventional diuretics:

1-oxo-3-(3-sulphamyl-4-chloro-phenyl)-3-hydroxyisoindoline, 6-chloro-7-sulphamyl-3,4-dihydro-1,2,4-benzothiadiazine 1,1-dioxide, 3-cyclopentylmethyl-6-chloro-7-sulphamyl-3,4-dihydro-1,2,4-benzothiadiazine 1,1-dioxide, 4-(2-methylenebutyryl)-2,3-dichloro-phenoxyacetic acid, 4-thenoyl-2,3-dichloro-phenoxyacetic acid, (1-oxo-2-methyl-2-phenyl-6,7-dichloro-5-indanyloxy)-acetic acid, 2-chloro-4-furfurylamino-5-carboxybenzenesulphonamide, 2-phenoxy-3-butylamino-5-carboxybenzenesulphonamide and 2-phenoxy-3-[3-(1-pyrrolyl)-propyl]-5-carboxybenzenesulphonamide.

In such pharmaceutical compositions and medicaments according to the invention the ratio of component A to component B, based on the particular mean effective dose, is from approximately 4:1 to approximately 1:4, preferably from approximately 3:2 to approximately 2:3. Since the mean effective dose of each specific component is a known value or a value that can easily be determined by known pharmacological test methods, it is easy for the person skilled in the art to prescribe a suitable ratio of the two components, within the limits mentioned above, for each patient according to the specific complaint, general state of health, individual responsiveness and age, and also the sex of the patient.

For example, such combination preparations contain, per dosage unit, from 5 to 150 mg, especially from 10 to 50 mg, of a compound of the formula I or a salt thereof as component A and, as component B, for example from 10 to 100 mg, especially from 25 to 50 mg, of 2-chloro-5-[3-hydroxy-1-oxo-isoindolyl-(3)]-benzenesulphonamide or 4-(2-methylenebutyryl)-2,3-dichlorophenoxyacetic acid, from 5 to 50 mg, especially from 12 to 25 mg, of 6-chloro-7-sulphamyl-3,4-dihydro-1,2,4-benzothiadiazine 1,1-dioxide or 2-chloro-4-furfurylamino-5-carboxybenzenesulphonamide, from 2 to 20 mg, especially from 5 to 10 mg, of 2-phenoxy-3-[3-(1-pyrrolyl)-propyl]-5-carboxybenzenesulphonamide, from 0.1 to 1.0 mg, especially from 0.25 to 0.5 mg, of 3-cyclopentylmethyl-6-chloro-7-sulphamoyl-3,4-dihydro-1,2,4-benzothiadiazine 1,1-dioxide or 2-phenoxy-3-butylamino-5-carboxybenzenesulphonamide, from 100 to 400 mg, especially 200 mg, of 4-thenoyl-2,3-dichlorophenoxyacetic acid and from 5 to 25 mg, especially 10 mg, of racemic (1-oxo-2-methyl-2-phenyl-6,7-dichloro-5-indanyloxy)-acetic acid, or half the amount of the laevo-form of this acid.

For the treatment of oedema in a moderately severe case, for example, from 1 to 3 dosage units are taken daily which contain the active ingredients in amounts by weight that are near the higher limit of the especially preferred dosage mentioned above; a moderately severe case of essential hypertonia is, for example, treated with from 1 to 3 dosage units the active ingredient content of which is near the lower limit of the especially preferred range.

The term "medicament" is used to denote individual separate portion of uniform composition which are suitable for medical administration. The expression "medicament in unit dosage form" is used in this description to denote individual separate portions of uniform composition which are suitable for medical administration and which each contain individually a specific amount of the active ingredient according to the invention corresponding to from approximately 0.05 to approximately 2, preferably from approximately 0.1 to approximately 1, daily dose(s).

The carriers for use in the pharmaceutical compositions are generally known materials.

The pharmaceutical compositions according to the invention contain preferably from approximately 0.1 to approximately 99.5% by weight, and especially from approximately 1 to approximately 90% by weight, of the active ingredient.

The recommended daily dosage of the active ingredient of the formula I (including salts) for a warm-blooded animal weighing 75 kg is approximately from 5 to 200 mg, preferably approximately from 10 to 100 mg, but may vary within wide limits depending on the species, age and individual responsiveness and may exceed the upper amount.

The pharmaceutical compositions, preparations, medicaments and medicaments in unit dosage form according to the invention which are mentioned above are prepared by means of conventional preparation processes of the pharmaceutical industry that are known per se, for example by means of customary mixing, granulating, tabletting, confectioning, dissolving and lyophilising processes, it being possible, if desired, for these processes to be carried out under aseptic conditions or for an intermediate or a finished product to be sterilised.

The present invention relates also to the use of the compounds of the formula I (including salts) for controlling very varied forms of hyperaldosteronism in humans and other warm-blooded animals, and also to a corresponding therapeutic method that is characterised by the administration of an effective dose of at least one of the active ingredients according to the invention on its own or together with one or more carriers or in a medicament form. The active ingredients according to the invention are administered enterally, for example rectally or, above all, orally, or parenterally, such as, especially, intravenously. A special method of carrying out the present treatment according to the invention is characterised in that a compound of the formula I according to the invention, or a salt thereof, as the aldosterone-antagonistic steroid component A, and a diuretic component which is non-specific with regard to electrolyte excretion (component B) are administered simultaneously or together, especially in the form of a corresponding pharmaceutical composition or in the form of a medicament.

In the following Examples, which further illustrate the invention without limiting the scope thereof, the temperatures are given in degrees Centigrade. All melting points are uncorrected.

EXAMPLE 1

75 mg of 90% m-chloroperbenzoic acid are added to a solution of 100 mg of 7α-methoxycarbonyl-20-spiroxa-4,9(11)-diene-3,21-dione in 2 ml of methylene chloride and the whole is left to stand for 18 hours at approximately 4° and then for a further 7 hours at room temperature. After diluting with methylene chloride, the mixture is washed in succession with 10% potassium iodide solution, 10% sodium thiosulphate solution, ice-cold saturated sodium bicarbonate solution and water, dried and concentrated by evaporation in a water-jet vacuum. The amorphous crude product is separated by preparative thin-layer chromatography over silica gel in the system methylene chloride/acetone (85:15). The main zone is eluted with 100 ml of ethyl acetate and concentrated by evaporation. The resulting crystalline 9α,11α-epoxy-7α-methoxycarbonyl-20-spirox-4-ene-3,21-dione is dissolved and allowed to crystallise from methylene chloride/ether. M.p. 239°–241°.

In an analogous manner, 7α-methoxycarbonyl-15β,16β-methylene-20-spiroxa-4,9(11)-diene-3,21-dione is converted into 9α,11α-epoxy-7α-methoxycarbonyl-15β,16β-methylene-20-spirox-4-ene-3,21-dione.

The starting material can be manufactured in the following manner:

(a) A solution of 3.54 ml of triethylaluminium in 9.66 ml of benzene is added over a period of 1.5 hours while cooling with ice and stirring with the exclusion of moisture to an ice-cold solution of 0.636 ml of anhydrous hydrocyanic acid in 6.44 ml of benzene, and the whole is then stirred for 16 hours at room temperature. The resulting diethylaluminium cyanide solution is added to a solution of 2.0 g of 20-spiroxa-4,6,9(11)-triene-3,21-dione [cf. J. Med. Chem., 6, 732–735 (1963)] in 40 ml of tetrahydrofuran, and the whole is heated under reflux for 30 minutes and cooled. The reaction solution is poured, while stirring, into 40 ml of 1N sodium hydroxide solution and extracted twice with ethyl acetate. The organic phase is washed in succession with saturated sodium chloride solution and ice-cold dilute hydrochloric acid, dried and concentrated by evaporation in a water-jet vacuum. The resulting oily crude product yields, after chromatography over silica gel by eluting with a mixture of hexane/ether/methanol (2:9:1), 7α-cyano-20-spiroxa-4,9(11)-diene-3,21-dione. M.p. 241°–243°.

In an analogous manner, 15β,16β-methylene-20-spiroxa-4,6,9(11)-triene-3,21-dione (see Example 7, manufacture of the starting materials) is converted into 7α-cyano-15β,16β-methylene-20-spiroxa-4,9(11)-diene-3,21-dione.

(b) 400 mg of 7α-cyano-20-spiroxa-4,9(11)-diene-3,21-dione from stage (a) are dissolved in 16 ml of benzene and, at a temperature of 10°, 4.8 ml of a 20% (w/v) solution of diisobutylaluminium hydride in toluene are added thereto and the whole is stirred for 30 minutes while cooling with ice. The mixture is heated to room temperature, stirred for a further 10 minutes, diluted with 8.0 ml of benzene and stirred again for a further 20 minutes at room temperature. While cooling with ice/sodium chloride, there are added dropwise to the reaction mixture, at an internal temperature of not more than 10°, first 4.8 ml of ethyl alcohol and then 48 ml of water, and the mixture is heated under reflux for 5 hours and then cooled. The mixture is acidified with ice-cold dilute hydrochloric acid and extracted with chloroform, and the organic phase is concentrated by evaporation in a water-jet vacuum.

In an analogous manner, there is obtained from 7α-cyano-15β,16β-methylene-20-spiroxa-4,9(11)-diene-3,21-dione the corresponding 7α-formyl-15β,16β-methylene-20-spiroxa-4,9(11)-diene-3,21-dione.

(c) The crude 7α-formyl-20-spiroxa-4,9(11)-diene-3,21-dione from stage (b) is dissolved in 20 ml of acetone and, at a temperature of 7°-10°, 1.2 ml of an 8N solution of chromium trioxide in aqueous sulphuric acid are added thereto and the whole is stirred for 1 hour while cooling with ice. The mixture is diluted with ice-water and extracted with chloroform, and the organic phase is washed once with water and extracted twice with 40 ml of saturated sodium bicarbonate solution each time. The combined alkaline extracts are acidified with 4N hydrochloric acid while cooling with ice and left to stand for 10 minutes. The product is taken up from the milky mixture in chloroform and, after being dried, concentrated by evaporation in a water-jet vacuum.

The resulting amorphous 3,21-dioxo-20-spiroxa-4,9(11)-diene-7α-carboxylic acid is further processed without additional purification.

In an analogous manner, there is obtained from 7α-formyl-15β,16β-methylene-20-spiroxa-4,9(11)-diene-3,21-dione3,21-dioxo-15β,16β-methylene-20-spiroxa-4,9(11)-diene-7α-carboxylic acid.

(d) An ethereal diazomethane solution is added dropwise to a solution of 235 mg of 3,21-dioxo-20-spiroxa-4,9(11)-diene-7α-carboxylic acid in 2.35 ml of methylene chloride until the evolution of nitrogen ceases. After 20 minutes at room temperature, the yellow reaction solution is carefully concentrated by evaporation and the residue is dissolved and allowed to crystallise once from methylene chloride/ether/petroleum ether to yield 7α-methoxycarbonyl-20-spiroxa-4,9(11)-diene-3,21-dione.
M.p. 205°-206°.

In an analogous manner, using 3,21-dioxo-15β,16β-methylene-20-spiroxa-4,9(11)-diene-7α-carboxylic acid as starting material the corresponding methyl ester thereof is obtained.

EXAMPLE 2

A mixture of 3.9 g of 7α-methoxycarbonyl-20-spiroxa-4,9(11)-diene-3,21-dione, 1.95 g of dipotassium hydrogen phosphate, 5.85 ml of trichloroacetonitrile, 17.5 g of 30% aqueous hydrogen peroxide solution and 89 ml of methylene chloride is intensively stirred at room temperature for 2 hours, diluted with further methylene chloride, washed in succession with 10% potassium iodide solution, 10% sodium thiosulphate solution, ice-cold saturated sodium bicarbonate solution and water, dried and concentrated by evaporation in a water-jet vacuum. The amorphous crude product is separated by preparative thin-layer chromatography over silica gel in the system methylene chloride/acetone (85:15). The main zone is eluted with 100 ml of ethyl acetate and concentrated by evaporation. The resulting crystalline 9α,11α-epoxy-7α-methoxycarbonyl-20-spirox-4-ene-3,21-dione of melting point 239°-241° is identical to the product of Example 1.

EXAMPLE 3

(a) A suspension of 13.0 g of 3,21-dioxo-20-spiroxa-4,9(11)-diene-7α-carboxylic acid (cf. Example 1c), 5.2 ml of 1,5-diazabicyclo(5,4,0)-undec-5-ene and 9.5 ml of isopropyl bromide in 80 ml of benzene is stirred under reflux for 3 hours. After cooling, 800 ml of saturated NaCl solution are added to the reaction mixture and the whole is extracted twice with ethyl acetate. The organic phases are washed in succession with dilute hydrochloric acid, dilute sodium hydroxide solution and saturated NaCl solution, dried and concentrated by evaporation. The crude product is chromatographed in chloroform over 30 times the amount by weight of silica gel. The uniform fractions yield, after being dissolved and allowed to crystallise from methylene chloride/ether, 3,21-dioxo-20-spiroxa-4,9(11)-diene-7α-carboxylic acid isopropyl ester.
M.p. 138°-139°.

(b) 0.5 ml of a solution of 1.1 g of dipotassium hydrogen phosphate in 2.5 ml of 30% hydrogen peroxide solution is added to a solution of 0.2 g of 3,21-dioxo-20-spiroxa-4,9(11)-diene-7α-carboxylic acid isopropyl ester in 1.6 ml of methylene chloride and 0.4 ml of trichloroacetonitrile, and the whole is stirred for 5 hours at 40°. After the addition of a further 0.4 ml of 30% hydrogen peroxide solution, stirring is continued for 21 hours at 40°. Customary working up yields an amorphous crude product which is chromatographed over 50 times the amount by weight of silica gel in the system methylene chloride/acetone (98:2). By crystallisation of the uniform fractions from methylene chloride/ether 9α,11α-epoxy-7α-isopropoxycarbonyl-20-spirox-4-ene-3,21-dione,
m.p. 207°-209°, is obtained.

EXAMPLE 4

(a) A suspension of 7.2 g of 3,21-dioxo-20-spiroxa-4,9(11)-diene-7α-carboxylic acid (cf. Example 1c), 2.88 ml of 1,5-diazabicyclo(5,4,0)-undec-5-ene and 5.6 ml of ethyl bromide in 43 ml of benzene is stirred under reflux for 3 hours. After cooling, 400 ml of saturated NaCl solution are added to the reaction mixture and the whole is extracted twice with ethyl acetate. The organic phases are washed in succession with dilute hydrochloric acid, dilute sodium hydroxide solution and saturated NaCl solution, dried and concentrated by evaporation. The crude product is chromatographed in chloroform over 30 times the amount by weight of silica gel. The uniform fractions yield, after being dissolved and allowed to crystallise from methylene chloride/ether, 3,21-dioxo-20-spiroxa-4,9(11)-diene-7α-carboxylic acid ethyl ester.
M.p. 128°-129°.

(b) A mixture of 1.93 g of 3,21-dioxo-20-spiroxa-4,9(11)-diene-7α-carboxylic acid ethyl ester, 19.3 ml of methylene chloride, 2.89 ml of trichloroacetonitrile, 365 ml of dipotassium hydrogen phosphate and 8.68 ml of 30% hydrogen peroxide solution is stirred for 6 hours at 40°. Customary working up yields an amorphous crude product which is chromatographed over 50 times the amount by weight of silica gel in the system methylene chloride/acetone (95:5). By crystallisation of the uniform fractions from methylene chloride/ether 9α,11α-epoxy-7α-ethoxycarbonyl-20-spirox-4-ene-3,21-dione, m.p. 177°–179°, is obtained.

EXAMPLE 5

430 mg of 90% m-chloroperbenzoic acid are added to a solution of 570 mg of 3,21-dioxo-20-spiroxa-4,9(11)-diene-7α-carboxylic acid (see Example 1c) in 11.4 ml of methylene chloride and the whole is left to stand at room temperature for 3 hours. While cooling with ice, an ethereal diazomethane solution is added to this mixture until no more nitrogen evolution can be seen. The reaction solution, diluted with methylene chloride, is washed in succession with a 10% potassium iodide solution, 10% sodium thiosulphate solution and ice-cold saturated sodium bicarbonate solution, dried and concentrated by evaporation in a water-jet vacuum. The gel-like crude product is chromatographed over 100 times the amount by weight of silica gel with a mixture of methylene chloride/acetone (96:4). The resulting 9α,11α-epoxy-7α-methoxycarbonyl-20-spirox-4-ene-3,21-dione is identical to the product of Example 1.

M.p. 239°–241° (after being dissolved and allowed to crystallise twice from methylene chloride/ether).

EXAMPLE 6

A solution of 980 mg of 3,21-dioxo-20-spiroxa-4,9(11)-diene-7α-carboxylic acid (cf. Example 1c) and 735 mg of 90% m-chloroperbenzoic acid in 19.6 ml of methylene chloride is left to stand at room temperature for 3 hours. After being diluted with methylene chloride, the mixture is washed in succession with 10% potassium iodide solution and 10% sodium thiosulphate solution and extracted with an ice-cold 0.5N sodium carbonate solution. The aqueous phase is washed with ether and freeze-dried. The pulverulent sodium salt of the 7α-carboxylic acid is suspended in 4.9 ml of dimethylformamide, 1.9 ml of isopropyl iodide are added thereto and the whole is stirred for 16 hours at 40°. Having been cooled, the reaction mixture is diluted with ice-water and acidified with dilute hydrochloric acid. The precipitate which forms is filtered with suction, washed with water and dissolved in methylene chloride; after being dried, the solution is concentrated by evaporation in a water-jet vacuum. The oily crude product yields, after being dissolved in methylene chloride, filtered through aluminium oxide (neutral) and concentrated by evaporation, amorphous 9α,11α-epoxy-7α-isopropoxycarbonyl-20-spirox-4-ene-3,21-dione which, after being dissolved and allowed to crystallise from methylene chloride/ether, melts at 207°–209°.

EXAMPLE 7

11.3 g of 80% p-nitroperbenzoic acid are added to a solution of 15.7 g of 6β,7β-methylene-20-spiroxa-4,9(11)-diene-3,21-dione in 628 ml of chloroform and the whole is left to stand at room temperature for 2 hours. After being diluted with methylene chloride, the mixture is washed in succession, once in each case, with 10% potassium iodide solution, 10% sodium thiosulphate solution and ice-cold dilute sodium hydroxide solution, and the organic phase, after being dried, is concentrated by evaporation in a water-jet vacuum. By chromatography over 150 times the amount by weight of silica gel and elution with a mixture of toluene/ethyl acetate (80:20) 9α,11α-epoxy-6β,7β-methylene-20-spirox-4-ene-3,21-dione is obtained which, after being dissolved and allowed to crystallise once from methylene chloride/ether, has a melting point of 299°–301°.

In an analogous manner, 6β,7β;15β,16β-bis-methylene-20-spiroxa-4,9(11)-diene-3,21-dione can be converted into 9α,11α-epoxy-6β,7β;15β,16β-bis-methylene-20-spirox-4-ene-3,21-dione.

The necessary starting materials can be manufactured in the following manner:

With the stringent exclusion of moisture, 4.37 g of a 72% (w/v) suspension of sodium hydride in mineral oil are added to a mixture of 30.4 g of trimethylsulphoxonium iodide and 102 ml of dimethyl sulphoxide and the whole is stirred for 1 hour at room temperature. 7.80 g of 20-spiroxa-4,6,9(11)-triene-3,21-dione [cf. J. Med.-Chem., 6, 732–735 (1963)] are added to this mixture and, after rinsing with 7.8 ml of dimethyl sulphoxide, the whole is stirred for 2 hours at room temperature. While stirring well, the reaction mixture is poured into ice-water, acidified with dilute hydrochloric acid and extracted twice with ethyl acetate. The organic phase is washed in succession with a saturated sodium chloride solution, ice-cold dilute sodium hydroxide solution and again with the sodium chloride solution, dried and concentrated by evaporation in a water-jet vacuum. The crude product is then chromatographed over 50 times the amount by weight of silica gel and eluted with a mixture of toluene/ethyl acetate (85:15). After evaporating off the solvents, 6β,7β-methylene-20-spiroxa-4,9(11)-diene-3,21-dione, m.p. 174°–178° (after being dissolved and allowed to crystallise twice from methylene chloride/ether), is obtained.

In an analogous manner, 6β,7β;15β,16β-bis-methylene-20-spiroxa-4,9(11)-diene-3,21-dione is also obtained using 15β,16β-methylene-20-spiroxa-4,6,9(11)-triene-3,21-dione as starting material; the latter can be obtained in the following manner:

(a) A solution of 20 g of 17α,20;20,21-bismethylenedioxypregn-5-ene-3β,11β-diol (U.S. Pat. No. 3,409,610) in 150 ml of pyridine and 150 g of acetic anhydride is heated under reflux for 1 hour. The cooled reaction solution is poured onto 3000 g of ice flakes while stirring and further stirred until thawing occurs. The precipitate is filtered with suction and dried in air, and the crude 3β,11β-diacetoxy-17α,20;20,21-bismethylenedioxypregn-5-ene is further processed without being purified.

(b) 20.3 g of the 3,11-diacetate which has been dried in air are introduced in portions, while stirring and with external cooling with ice-water, into 71 ml of a solution prepared beforehand by passing, at approximately 0°, 141 g of gaseous hydrogen fluoride into a solution consisting of 100 ml of isopropyl alcohol, 48 g of urea and 9.6 ml of water.

The reaction mixture is stirred for 1 hour while cooling with ice-water, carefully poured into an ice-cold solution of 142 g of sodium sulphite in 1015 ml of water and stirred for 20 minutes. The mixture is extracted with ethyl acetate and washed in succession with saturated sodium chloride solution, ice-cold dilute hydrochloric acid, ice-cold dilute sodium hydroxide solution and again with dilute sodium chloride solution, dried and concentrated by evaporation in a water-jet vacuum. The residue is chromatographed over 10 times the amount by weight of silica gel. By elution with a mixture of methylene chloride/acetone (95:5) uniform fractions are obtained which, after being dissolved and allowed to crystallise once from methylene chloride/methanol/ether, yield $3\beta,11\beta$-diacetoxy-$17\alpha,21$-dihydroxypregn-5-en-20-one of melting point 231°–233°.

(c) To a solution of 13.8 g of the last-mentioned compound in 207 ml of dioxan there are added 69 g of finely pulverulent manganese dioxide and the whole is boiled under reflux for 3 hours. After cooling to room temperature, the solid portion is removed by filtering with suction and is washed well with chloroform. The filtrate is concentrated by evaporation, dissolved in methylene chloride and filtered through 10 times the amount by weight of neutral aluminium oxide. By evaporating off the solvent, crystalline $3\beta,11\beta$-diacetoxy-androst-5-en-17-one is obtained which, after being recrystallised once from methylene chloride/petroleum ether, melts at 177°–179°.

(d) A mixture of 7.5 g of $3\beta,11\beta$-diacetoxy-androst-5-en-17-one and 150 mg of p-toluenesulphonic acid in 450 ml of benzene and 7.5 ml of ethylene glycol is boiled under reflux for 16 hours on a water separator. After cooling, the solution is diluted with ethyl acetate and immediately washed with 225 ml of ice-cold saturated sodium chloride solution. The organic phase, after being dried, is concentrated by evaporation in a water-jet vacuum and the oily $3\beta,11\beta$-diacetoxy-17,17-ethylenedioxy-androst-5-ene is used for the next stage without being purified.

(e) To a stirred suspension of 2.35 g of lithium aluminium hydride in 95 ml of tetrahydrofuran there is added dropwise, at an internal temperature of 5°–10°, a solution of 4.7 g of $3\beta,11\beta$-diacetoxy-17,17-ethylenedioxy-androst-5-ene in 140 ml of tetrahydrofuran, rinsing out is effected with 9 ml of tetrahydrofuran and the mixture is boiled under reflux for 12 hours. The reaction mixture is then decomposed at an internal temperature of not more than 5° by the careful dropwise addition of a mixture of 9 ml of tetrahydrofuran and 14 ml of ethyl acetate and then a mixture of 9 ml of tetrahydrofuran and 14 ml of water, and, after the addition of 70 g of anhydrous sodium sulphate, is stirred for a further 30 minutes without cooling. Solid portions are removed by filtration with suction over a layer of kieselguhr (washing with tetrahydrofuran), and the filtrate is concentrated in a water-jet vacuum. The amorphous residue is chromatographed over 50 times the amount by weight of silica gel. By elution with a mixture of methylene chloride/acetone (93:7) and evaporation of the solvent uniform 17,17-ethylenedioxy-androst-5-ene-$3\beta,11\beta$-diol is obtained which, after being dissolved and allowed to crystallise once from methylene chloride/ether, melts at 123°–125°.

(f) 36.3 g of pyridine hydrobromide perbromide are added to a solution of 16.8 g of 17,17-ethylenedioxy-androst-5-ene-$3\beta,11\beta$-diol in 102 ml of tetrahydrofuran and the whole is stirred at room temperature for 2½ hours. 26.9 g of sodium iodide are added to the mixture, stirring is carried out for a further 30 minutes, a solution of 36.3 g of sodium thiosulphate in 50.4 ml of water and 100 ml of pyridine are added in succession and the whole is again stirred at room temperature for 2 hours. The reaction mixture is diluted with 100 ml of water and concentrated at approximately 45° in a water-jet vacuum. The residue is taken up in ethyl acetate and washed in succession with saturated sodium chloride solution, ice-cold dilute hydrochloric acid, ice-cold dilute sodium hydroxide solution and again with saturated sodium chloride solution and dried over sodium sulphate. By distilling off the solvents in a water-jet vacuum an amorphous residue of crude 16α-bromo-17,17-ethylenedioxy-androst-5-ene-$3\beta,11\beta$-diol is obtained. The resulting crude product (13 g) is dissolved in 143 ml of dimethyl sulphoxide and, in the course of 30 minutes at 45° while stirring, a mixture of 7 g of potassium tert.-butoxide in 13 ml of dimethyl sulphoxide is added thereto and the whole is stirred for 20 hours at 50° (bath temperature). The mixture is cooled to room temperature, diluted with approximately 1300 ml of a saturated ammonium chloride solution and taken up in ethyl acetate; the organic phase is washed three times with a saturated sodium chloride solution and dried over sodium sulphate. By distilling off the solvents in a water-jet vacuum amorphous 17,17-ethylenedioxy-androsta-5,15-diene-$3\beta,11\beta$-diol is obtained the purity of which is adequate for further processing.

(g) 4 ml of a solution of 100 mg of p-toluenesulphonic acid in 10 ml of water are added to a solution of 800 mg of 17,17-ethylenedioxy-androsta-5,15-diene-$3\beta,11\beta$-diol in 40 ml of acetone and the whole is stirred for 6 hours at room temperature. After diluting with 40 ml of water, the acetone is distilled off in a water-jet vacuum and the oily residue is taken up in chloroform and washed once with ice-cold saturated sodium bicarbonate solution. After evaporating off the organic solvents, amorphous $3\beta,11\beta$-dihydroxy-androsta-5,16-dien-17-one is obtained which can be used for the next stage without further purification.

(h) 1.52 g of 55–60% strength sodium hydride (as a mineral oil suspension) and 7.57 g of trimethylsulphoxonium iodide are added under a nitrogen atmosphere to dimethyl sulphoxide (64 ml) and the whole is stirred first at room temperature for 30 minutes and then at an external temperature of 34°–40° for a further 30 minutes. There are added to the reaction mixture, which has been cooled to room temperature, 8 g of $3\beta,11\beta$-dihydroxy-androsta-5,15-dien-17-one and rinsing out is effected with 26 ml of dimethyl sulphoxide. The reaction mixture is stirred for 3 hours at room temperature, poured onto 1 liter of ice-cold saturated sodium chloride solution, rinsed out with a little methyl alcohol and water, acidified with dilute hydrochloric acid and stirred for 30 minutes. The oil which has separated is taken up in ethyl acetate and the organic phase is washed in succession with saturated sodium chloride solution, ice-cold dilute sodium hydroxide solution and again with saturated sodium chloride solution. After drying, the solvents are evaporated off in a water-jet vacuum and the resulting amorphous $3\beta,11\beta$-dihydroxy-$15\beta,16\beta$-methylene-androst-5-en-17-one is subjected to the subsequent acetylation without being purified.

(i) A solution of 7.9 g of $3\beta,11\beta$-dihydroxy-$15\beta,16\beta$-methylene-androst-5-en-17-one in 39.5 ml of pyridine and 39.5 ml of acetic anhydride is left to stand at room temperature for 5 hours, diluted with 800 ml of ice-water and, after standing for 1 hour, extracted with ethyl acetate. The organic phase is washed in succession with saturated sodium chloride solution, ice-cold dilute hydrochloric acid, ice-cold dilute sodium hydroxide solution and again with saturated sodium chloride solution, dried and concentrated in a water-jet vacuum. By chromatography of the crude product over 30 times the amount by weight of silica gel and elution with a mixture of methylene chloride/acetone (98:2) 3β-acetoxy-11β-hydroxy-15β,16β-methylene-androst-5-en-17-one is obtained which, after being dissolved and allowed to crystallise once from methylene chloride/ether/petroleum ether, melts at 209°–211°.

(j) 2.6 ml of a solution of 5% by weight sulphur dioxide in methanesulphonic acid chloride are added to a solution of 1.75 g of 3β-acetoxy-11β-hydroxy-15β,16β-methylene-androst-5-en-17-one in 10.5 ml of dimethylformamide and 3.5 ml of γ-collidine and the whole is stirred for 20 minutes, the internal temperature being allowed to increase to approximately 45°. The mixture together with the precipitate which has separated is poured, while stirring, onto 17.5 ml of ice-water and stirred for a further 10 minutes. The oil which has separated is taken up in ethyl acetate and washed in succession with saturated sodium chloride solution, ice-cold dilute hydrochloric acid, ice-cold dilute sodium hydroxide solution and again with saturated sodium chloride solution. After evaporating off the solvents, 3β-acetoxy-15β,16β-methylene-androsta-5,9(11)-dien-17-one that is uniform according to thin-layer chromatography is obtained and is further processed without being purified.

(k) While cooling with ice-water, there are added to a solution of 5.2 g of 3β-acetoxy-15β,16β-methylene-androsta-5,9(11)-dien-17-one in 127.5 ml of tetrahydrofuran 1.78 g of lithium wire (pieces of approximately 5 mm in length) and then, over a period of 10 minutes, a solution of 12.75 ml of the cyclic ethylene acetal of β-chloropropionaldehyde in 12.75 ml of tetrahydrofuran is added dropwise thereto; the whole is then stirred for 1 hour while cooling with ice and for 16 hours at room temperature. 330 ml of ethyl acetate are added to the reaction mixture which is stirred for 45 minutes, then diluted with further ethyl acetate, washed in succession with saturated sodium chloride solution, ice-cold dilute hydrochloric acid, ice-cold dilute sodium hydroxide solution and again with saturated sodium chloride solution, dried and concentrated in a water-jet vacuum. The oily crude product is dissolved in a mixture of toluene/ethyl acetate (90:10) and filtered through 10 times the amount of weight of silica gel. After evaporating off the solvents, the filtrate yields 4.84 g of amorphous substance. This is dissolved in 363 ml of chloroform, 242 g of acidic aluminum oxide (activity stage 1) are added and the whole is stirred at reflux temperature for 2½ hours, diluted with a further 363 ml of chloroform, stirred for a further 5 minutes and cooled. The mixture is filtered with suction over kieselguhr, the filter cake is washed with chloroform and the filtrate is concentrated in a water-jet vacuum. The resulting crude 21-carbaldehyde (4 g) is dissolved in 20 ml of methylene chloride and 80 ml of acetone, and 8 ml of an 8N chromium(VI)-sulphuric acid solution are added thereto at 5° over a period of 5 minutes and the mixture is stirred for 45 minutes while cooling with ice. The mixture is diluted with 80 ml of ice-cold water, stirred for 10 minutes without cooling and extracted with methylene chloride. The organic phase is washed with ice-cold saturated sodium bicarbonate solution and dried. By distilling off the solvents in a water-jet vacuum a crystalline crude product is obtained which, in a solution in methylene chloride, is filtered through 5 times the amount by weight of neutral aluminium oxide. By distilling off the solvent from the main fraction crystals are obtained which, after being dissolved and allowed to crystallise once from methylene chloride/ether, yield 3β-acetoxy-15β,16β-methylene-20-spiroxa-5,9(11)-dien-21-one of melting point 241°–243°.

(l) 19 ml of a 1N sodium hydroxide solution are added to a suspension of 1.9 g of 3β-acetoxy-15β,16β-methylene-20-spiroxa-5,9(11)-dien-21-one in 26.6 ml of chloroform and 190 ml of methyl alcohol. The mixture is stirred for 1 hour at room temperature, diluted with 190 ml of water and extracted with one portion of chloroform and one portion of a mixture of chloroform/methanol (90:10). The combined organic phase, after being dried, are concentrated in a water-jet vacuum and the crystalline crude product is recrystallised once from methylene chloride/ether/petroleum ether. The reslting 3β-hydroxy-15β,16β-methylene-20-spiroxa-5,9(11)-dien-21-one melts at 244°–246°.

(m) 4 ml of solvent are distilled off under normal pressure from a suspension of 400 mg of 3β-hydroxy-15β,16β-methylene-20-spiroxa-5,9(11)-dien-21-one in 20 ml of toluene and 3 ml of cyclohexanone. Cooling is effected to an internal temperature of approximately 80°, 480 mg of aluminium propoxide are added and the whole is stirred under reflux for 2 hours. The solution is cooled to room temperature, a solution of 0.4 ml of acetic acid in 0.8 ml of toluene is added thereto and the solution is evaporated to dryness four times in a water-jet vacuum with 5 ml of water each time. The oily residue is taken up in chloroform and washed in succession with ice-cold dilute hydrochloric acid, water, ice-cold sodium hydroxide solution and again with water, and the organic phase is dried and evaporated in a water-jet vacuum. The amorphous crude product is applied to 50 times the amount by weight of silica gel an chromatographed with a mixture of methylene chloride/acetone (98:2). The resulting 15β,16β-methylene-20-spiroxa-4,9(11)-diene-3,21-dione melts at 172°–174° after being dissolved and allowed to crystallise once from methylene chloride/ether/petroleum ether.

(n) A solution of 3.27 g of 15β,16β-methylene-20-spiroxa-4,9(11)-diene-3,21-dione in 16.35 ml of dioxan and 6.54 ml of orthoformic acid trimethyl ester is mixed with 0.654 ml of a solution of 900 mg of p-toluenesulphonic acid in 10 ml of dioxan and 2 ml of ethyl alcohol, the mixture is stirred for 4 hours at room temperature, poured, while stirring, into 430 ml of an ice-cold 0.2N sodium hydroxide solution and intensively stirred for 15 minutes. The precipitate is filtered with suction, washed with water and dried on the suction filter. The resulting crude 3-ethoxy-15β,16β-methylene-20-spiroxa-3,5,9(11)-trien-21-one is dissolved in 105 ml of acetone and treated in succession with a solution of 1.13 g of sodium acetate (trihydrate) in 8.84 ml of water and, while cooling to −5°, with 1.55 g of N-bromoacetamide and 1.13 ml of acetic acid. The mixture is stirred for 30 minutes at an internal temperature of approximately −3° and subsequently for a further 15 minutes without cooling, a solution of 0.88 g of potassium iodide in 17.7 ml of water and a solution of 5.58 g of sodium thiosulphate in 17.7 ml of water are added in succession thereto, and the mixture is stirred for a further 5 minutes and diluted with 88 ml of water. The mixture is extracted with chloroform and the organic phase is washed with ice-cold saturated sodium bicarbonate solution. Drying and concentration of the organic phase produces the amorphous residue which, dissolved in 78 ml of dimethylformamide, has added to it 3.89 g of lithium carbonate and 3.89 g of lithium bromide and is stirred for 3 hours at 100°. Having been cooled, the mixture is poured, while stirring, onto 750 ml of ice-water, and the precipitate is filtered with suction and washed with water. The filter cake is dissolved in chloroform, dried with sodium sulphate and evaporated to dryness in a water-jet vacuum. A solution of the resulting residue in methylene chloride is filtered through a column of neutral aluminium oxide (activity II) and eluted with further portions of the same solvent. The eluates are concentrated and the desired $15\beta,16\beta$-methylene-20-spiroxa-4,6,9(11)-triene-3,21-dione is precipitated in amorphous form by the addition of ether. The product is uniform according to thin-layer chromatography and is suitable for further processing.

EXAMPLE 8

A mixture of 2.0 g of $9\alpha,11\alpha$-epoxy-$6\beta,7\beta$-methylene-20-spirox-4-ene-3,21-dione, 40 ml of methyl alcohol and 2.45 ml of a 2N aqueous solution of potassium hydroxide is stirred for 16 hours at 60°. The reaction solution is concentrated by evaporation in a water-jet vacuum and freed of residual water by being concentrated by evaporation three times with absolute ethyl alcohol. The residue is dissolved in hot methanol and precipitated in crystalline form with ethyl acetate. The resulting potassium $9\alpha,11\alpha$-epoxy-$17\beta$-hydroxy-$6\beta,7\beta$-methylene-3-oxo-$17\alpha$-pregn-4-ene 21-carboxylate is dried in a high vacuum at 80°.

Analysis: calculated 8.83% K.; found 8.76% K.

The same potassium salt is obtained with an analogous procedure and using, as starting material, an equivalent amount of $9\alpha,11\alpha$-epoxy-$17\beta$-hydroxy-$6\beta,7\beta$-methylene-3-oxo-$17\alpha$-pregn-4-ene-21-carboxylic acid methyl ester.

In an analogous manner, $9\alpha,11\alpha$-epoxy-$6\beta,7\beta;15\beta,16\beta$-bis-methylene-20-spirox-4-ene-3,21-dione or $9\alpha,11\alpha$-epoxy-$17\beta$-hydroxy-$6\beta,7\beta;15\beta,16\beta$-bis-methylene-3-oxo-$17\alpha$-pregn-4-ene-21-carboxylic acid methyl ester can also be converted into the potassium salt of the last-mentioned acid.

EXAMPLE 9

1.5 ml of 4N methanolic potassium hydroxide solution are added to a suspension of 1.8 g of $9\alpha,11\alpha$-epoxy-$6\beta,7\beta$-methylene-20-spirox-4-ene-3,21-dione in 18 ml of methyl alcohol and the whole is boiled under reflux for 1 hour. At normal pressure, approximately 12 ml of the solvent are distilled off, 18 ml of ethyl acetate are added and the mixture is concentrated to approximately 12 ml in a water-jet vacuum. After adding a further 18 ml of ethyl acetate, the crystalline precipitate which has formed is stirred for a further 10 minutes, filtered with suction, washed with ethyl acetate and ether and dried on the suction filter. The yellowish powder is dissolved in 9 ml of dimethylformamide, 0.9 ml of methyl iodide is added thereto and the mixture is stirred at room temperature in a closed vessel. The mixture is diluted with ice-water and stirred for 15 minutes. The precipitate which has separated is filtered with suction, washed out with water and dissolved in chloroform and the organic phase, after being dried, is concentrated by evaporation in a water-jet vacuum. The amorphous crude product is applied to 30 times the amount by weight of silica gel and eluted with a mixture of methylene chloride/acetone (95:5). The combined uniform fractions yield, after being dissolved and allowed to crystallise once from methylene chloride/ether, $9\alpha,11\alpha$-epoxy-$17\beta$-hydroxy-$6\beta,7\beta$-methylene-3-oxo-$17\alpha$-pregn-4-ene-21-carboxylic acid methyl ester. M.p. 189°–191°.

In an analogous manner, in place of methyl iodide, reaction can be carried out with an equivalent amount of dimethyl sulphate.

EXAMPLE 10

A solution of 1.3 g of $9\alpha,11\alpha$-epoxy-$6\beta,7\beta$-methylene-20-spirox-4-ene-3,21-dione and 1.3 g of DDQ (2,3-dichloro-5,6-dicyanobenzoquinone) in 26 ml of dioxan is stirred for 15 hours at 100°. The dark reaction mixture is concentrated by evaporation three times with toluene in a water-jet vacuum, and the residue is dissolved in methylene chloride and filtered through 10 times the amount by weight of aluminium oxide (neutral). The resulting crystals yield, after being dissolved and allowed to crystallise once from methylene chloride/ether, the desired $9\alpha,11\alpha$-epoxy-$6\beta,7\beta$-methylene-20-spiroxa-1,4-diene-3,21-dione of melting point 295°–296°.

EXAMPLE 11

A mixture of 1.3 g of $9\alpha,11\alpha$-epoxy-$7\alpha$-methoxycarbonyl-20-spirox-4-ene-3,21-dione, 17 ml of methyl alcohol and 1.41 ml of a 2N aqueous solution of potassium hydroxide is stirred for 16 hours at room temperature and then for 20 minutes at 60°. The reaction solution is concentrated by evaporation in a water-jet vacuum and freed of residual water by being concentrated by evaporation three times with absolute ethyl alcohol. The crystalline residue is stirred with 40 ml of ethyl acetate, filtered with suction and washed out on the filter with ethyl acetate and ether. The resulting flaky potassium $9\alpha,11\alpha$-epoxy-$17\beta$-hydroxy-$7\alpha$-methoxycarbonyl-3-oxo-$17\alpha$-pregn-4-ene-21-carboxylate is dried in a high vacuum at 80°.

Analysis: calculated 8.31% K; found 8.02% K.

The same salt is also obtained by analogous reaction of an equivalent amount of $9\alpha,11\alpha$-epoxy-$17\beta$-hydroxy-3-oxo-$17\beta$-pregn-4-ene-$7\alpha$,21-dicarboxylic acid dimethyl ester.

EXAMPLE 12

A mixture of 1.25 g of $9\alpha,11\alpha$-epoxy-$7\alpha$-isopropoxycarbonyl-20-spirox-4-ene-3,21-dione, 15.6 ml of methyl alcohol and 1.27 ml of a 2N aqueous solution of potassium hydroxide is stirred for 16 hours at room temperature and then for 20 minutes under reflux. The reaction solution is concentrated by evaporation in a water-jet vacuum and freed of residual water by being concentrated by evaporation three times with absolute ethyl alcohol. The crystalline residue is stirred with 40 ml of ethyl acetate, filtered with suction and washed out on the filter with ethyl acetate and ether. The resulting flaky potassium $9\alpha,11\alpha$-epoxy-$17\beta$-hydroxy-$7\alpha$-isopropoxycarbonyl-3-oxo-$17\alpha$-pregn-4-ene 21-carboxylate is dried in a high vacuum at 80°.

Analysis: calculated 7.66% K.; found 7.15% K.

In an analogous manner, using an equivalent amount of 9α,11α-epoxy-7α-ethoxycarbonyl-20-spirox-4-ene-3,21-dione or 9α,11α-epoxy-17β-hydroxy-3-oxo-17β-pregn-4-ene-7α,21-dicarboxylic acid 7-ethyl ester 21-methyl ester as starting material, the potassium salt of 9α,11α-epoxy-7α-ethoxycarbonyl-17β-hydroxy-3-oxo-17β-pregn-4-ene-21-carboxylic acid is obtained the analysis (potassium content) of which corresponds to the theoretical analysis.

EXAMPLE 13

With the stringent exclusion of moisture, a mixture of 5.7 g of trimethylsulphoxonium iodide in 19 ml of dimethyl sulphoxide is stirred for 1 hour at room temperature with 0.82 g of a 72% (wt/v) suspension of sodium hydride in mineral oil, and 1.46 g of 9α,11α-epoxy-20-spiroxa-4,6-diene-3,21-dione [cf. J. Med. Chem., 6, 732–735 (1963)] are added thereto, rinsing out is effected with 1.46 ml of dimethyl sulphoxide and stirring is continued for 3.5 hours at room temperature. The reaction mixture is diluted with 146 ml of ice-water, acidified with dilute hydrochloric acid and extracted with ethyl acetate. The organic phase is washed in succession with saturated sodium chloride solution, ice-cold dilute sodium hydroxide solution and again with saturated sodium chloride solution, dried over sodium sulphate and concentrated by evaporation in a water-jet vacuum. The resulting amorphous crude product is chromatographed over 100 times the amount by weight of silica gel. By eluting with a mixture of toluene/acetone (95:5) and concentrating by evaporation 9α,11α-epoxy-6α,7α-methylene-20-spirox-4-ene-3,21-dione, m.p. 262°–264° (after being dissolved and allowed to crystallise once from methylene chloride/ether), is obtained.

EXAMPLE 14

A mixture of 10 g of 9α,11α-epoxy-7α-methoxycarbonyl-20-spirox-4-ene-3,21-dione, 100 ml of methyl alcohol and 7.5 ml of a 4N methanolic solution of potassium hydroxide is boiled under reflux for one hour. At normal pressure, approximately 80 ml are distilled off from the reaction mixture, 60 ml of ethyl acetate are added and the suspension is concentrated to approximately 20 ml in a water-jet vacuum. After diluting again with 60 ml of ethyl acetate, the mixture is left to stand at room temperature for 30 minutes, whereupon the precipitate is filtered with suction and washed out twice with ether. The pulverulent residue is suspended in 46 ml of dimethylformamide and, after the addition of 4.6 ml of methyl iodide, stirred in a closed vessel for 40 hours at room temperature. After diluting with 300 ml of ice-water, the precipitate is separated off, washed with water, dissolved in ethyl acetate and the solution, after being dried, is concentrated by evaporation in a water-jet vacuum. The resulting crude product is chromatographed over 30 times the amount of silica gel. The uniform fractions eluted with a mixture of methylene chloride/acetone (92:8) yield, after sprinkling with ether and precipitation of the resulting precipitate once from methylene chloride with ether, the desired 9α,11α-epoxy-17β-hydroxy-3-oxo-17α-pregn-4-ene-7α,21-dicarboxylic acid dimethyl ester in amorphous form.

In an analogous manner, 9α,11α-epoxy-7α-methoxy-15β,16β-methylene-20-spirox-4-ene-3,21-dione can be converted into 9α,11α-epoxy-17β-hydroxy-15β,16β-methylene-3-oxo-17α-pregn-4-ene-7α,21-dicarboxylic acid dimethyl ester.

EXAMPLE 15

Tablets, each containing approximately 20 mg of active ingredient, for example 9α,11α-epoxy-7α-methoxycarbonyl-20-spirox-4-ene-3,21-dione or 9α,11α-epoxy-6β,7β-methylene-20-spirox-4-ene-3,21-dione, are prepared as follows:

| Composition for 1000 tablets | |
|---|---|
| active ingredient, very finely ground | 20.0 g |
| powdered sugar (saccharose) | 79.0 g |
| gum arabic | 4.75 g |
| sorbitol | 3.75 g |
| talc | 2.5 g |
| magnesium stearate | 4.9 g |
| mineral oil | 0.1 g |
| carboxymethylcellulose (sodium salt) | 5.0 g |

Preparation

The active ingredient is mixed with the powdered sugar and gum arabic, sieved and granulated by means of an approximately 35 percent aqueous sorbitol solution. The granulate is forced through a sieve, dried and again sieved, and intimately mixed with the remaining adjuncts (talc, magnesium stearate, mineral oil and carboxymethylcellulose sodium salt). The mixture is pressed in the usual manner to form tablets of 120 mg.

EXAMPLE 16

Gelatine capsules, each containing approximately 25 mg of active ingredient, for example 9α,11α-epoxy-6β,7β-methylene-20-spirox-4-ene-3,21-dione, are prepared in the following manner:

| Composition for 1000 capsules | |
|---|---|
| active ingredient, very finely ground | 25 g |
| lactose, very finely ground | 25 g |

The active ingredient and the lactose are intimately mixed, triturated and sieved, and the resulting powder is introduced into gelatine capsules in portions of 50 mg each.

EXAMPLE 17

Tablets, each containing approximately 25 mg of component A and approximately 25 mg of component B, are prepared in the following manner:

| Composition of one tablet: | |
|---|---|
| component A, micronised | 25.0 mg |
| component B, micronised | 25.0 mg |
| corn starch | 50.0 mg |
| silica, colloidal | 5.0 mg |
| gelatine | 5.0 mg |
| cellulose, microcrystalline | 75.0 mg |
| sodium carboxymethyl starch | 20.0 mg |
| magnesium stearate | 1.5 mg |
| | 306.5 mg |

Preparation of 100,000 tablets 2.5 kg of component A, micronised, 2.5 kg of component B, micronised, and 5.0 kg of corn starch are mixed with 0.5 kg of colloidal silica and worked up with a solution of 0.5 kg of gelatine in 5.0 kg of distilled water (30° C.) to form a moist mass. This is forced through a sieve of 3 mm mesh width and dried at 45° C. (fluidised-bed drier). The granulate is forced through a sieve of 0.8 mesh width, mixed with a previously sieved mixture of 7.5 kg of microcrystalline cellulose and 2.0 kg of sodium carboxymethyl starch and also 0.15 kg of magnesium stearate and pressed to form tablets weighing 306.5 mg.

As component A there is used, for example, $9\alpha,11\alpha$-epoxy-$7\alpha$-(methoxycarbonyl or isopropoxycarbonyl)-20-spirox-4-ene-3,21-dione, $9\alpha,11\alpha$-epoxy-$6\beta,7\beta$-methylene-20-spirox-4-ene-3,21-dione or $9\alpha,11\alpha$-epoxy-$6\beta,7\beta;15\beta,16\beta$-bis-methylene-20-spirox-4-ene-3,21-dione and, as component B, 6-chloro-7-sulphamyl-3,4-dihydro-1,2,4-benzothiadiazine 1,1-dioxide.

In an analogous manner, the following active ingredients may also be used in equivalent amounts:
as component A:
the potassium or sodium salt of $9\alpha,11\alpha$-epoxy-$17\beta$-hydroxy-$6\beta,7\beta$-methylene-3-oxo-$17\alpha$-pregn-4-ene-21-carboxylic acid (50 mg) or $9\alpha,11\alpha$-epoxy-$17\beta$-hydroxy-$7\alpha$-methoxycarbonyl-3-oxo-$17\alpha$-pregn-4-ene-21-carboxylic acid (30 mg);
as component B:
2-chloro-5-(3-hydroxy-1-oxo-isoindolyl-3)-benzenesulphonamide or 4-(2-methylenebutyryl)-2,3-dichloro-phenoxyacetic acid (50 mg of each), 6-chloro-7-sulphamyl-3,4-dihydro-1,2,4-benzothiadiazine 1,1-dioxide (25 mg), 2-phenoxy-3-butylamino-5-carboxybenzenesulphonamide (0.5 mg), (1-oxo-2-methyl-2-phenyl-6,7-dichloro-indanyl-5-oxy)-acetic acid (as racemate 20 mg, as the laevo-form 10 mg) or 3-cyclopentylmethyl-6-chloro-7-sulphamyl-3,4-dihydro-1,2,4-benzothiadiazine 1,1-dioxide (0.5 mg).

We claim:
1. A steroid compound of the formula

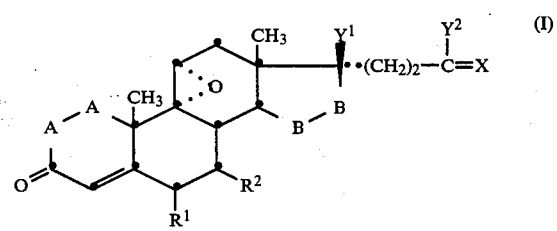

in which
—A—A— represents the group —CH$_2$—CH$_2$— or —CH=CH—,
R$^1$ represents hydrogen, and
R$^2$ represents an $\alpha$-oriented lower alkoxycarbonyl radical, or
R$^1$ and R$^2$ together represent an $\alpha$- or a $\beta$-oriented methylene radical,
—B—B— represents the group —CH$_2$—CH$_2$— or an $\alpha$- or $\beta$-oriented group

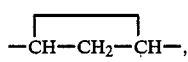

X represents two hydrogen atoms or oxo,
Y$^1$ and Y$^2$ together represent the oxygen bridge —O—, or
Y$^1$ represents hydroxy, and
Y$^2$ represents hydroxy, lower alkoxy or, if X represents H$_2$, also lower alkanoyloxy,
and salts of compounds in which X represents oxo and Y$^2$ represents hydroxy.

2. A compound according to claim 1, in which R$^2$ represents methoxycarbonyl, ethoxycarbonyl or isopropoxycarbonyl.

3. A compound according to claim 1, in which R$^1$ and R$^2$ together represent a $\beta$-oriented methylene radical.

4. A compound according to claim 1, in which —B—B— represents the $\beta$-oriented group

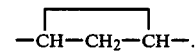

5. A compound according to claim 1, in which X represents oxo.

6. A compound according to claim 1, in which Y$^1$ and Y$^2$ together represent the oxygen bridge —O—.

7. A compound according to claim 1, in which R$^1$ and R$^2$ together represent a methylene group, X represents oxo and each of Y$^1$ and Y$^2$ represents hydroxy.

8. An alkali metal salt of a compound according to claim 7.

9. A potassium salt of a compound according to claim 7.

10. A compound according to claim 1, which is $9\alpha,11\alpha$-epoxy-$7\alpha$-methoxycarbonyl-20-spirox-4-ene-3,21-dione.

11. A compound according to claim 1, which is $9\alpha,11\alpha$-epoxy-$7\alpha$-isopropoxycarbonyl-20-spirox-4-ene-3,21-dione.

12. A compound according to claim 1, which is $9\alpha,11\alpha$-epoxy-$6\alpha,7\alpha$-methylene-20-spirox-4-ene-3,21-dione.

13. A compound according to claim 1, which is $9\alpha,11\alpha$-epoxy-$6\beta,7\beta$-methylene-20-spirox-4-ene-3,21-dione.

14. A pharmaceutical composition containing as active ingredient one of the compounds defined in claim 1.

15. A pharmaceutical composition containing an effective amount of an aldosterone-antagonistic compound according to claim 1, and at least one diuretic which is non-specific with regard to electrolytes and which increases diuresis by renal and by extrarenal action on tissue.

16. A therepeutic method for controlling hyperaldosteronism in humans and other warm-blooded animals, comprising the administration of an effective amount of a compound according to claim 1, in the presence or absence of a pharmaceutically acceptable carrier.

17. A therapeutic method for controlling hyperaldosteronism in humans and other warm blooded animals, comprising the simultaneous administration of an effective amount of a compound according to claim 1, together with at least one diuretic which is non-specific with regard to electrolytes and which increases diuresis by renal and by extrarenal action on tissue.

* * * * *